United States Patent [19]

Rutishauser et al.

[11] 4,092,121

[45] May 30, 1978

[54] TITRATION APPARATUS

[75] Inventors: Heinz Rutishauser, Greifensee; Otakar Siroky, Bottmingen, both of Switzerland

[73] Assignee: Mettler Instrumente AG, Zurich, Switzerland

[21] Appl. No.: 789,263

[22] Filed: Apr. 20, 1977

[30] Foreign Application Priority Data

Jun. 9, 1976 Switzerland .......................... 7231/76

[51] Int. Cl.² ............................................ G01N 31/16
[52] U.S. Cl. .............................. 23/253 R; 204/195 T; 364/497
[58] Field of Search ................. 23/253 R, 259, 230 R; 204/195 T, 1 T; 364/498, 497

[56] References Cited

U.S. PATENT DOCUMENTS

| 3,879,604 | 4/1975 | Malmvig ............................. 23/253 X |
| 3,882,318 | 5/1975 | Mioduski ............................ 23/253 X |
| 4,018,565 | 4/1977 | Fletcher et al. .................... 23/253 R |
| 4,026,665 | 5/1977 | Mansfield ........................ 204/195 T |

Primary Examiner—R.E. Serwin
Attorney, Agent, or Firm—Werner W. Kleeman

[57] ABSTRACT

A titration apparatus incorporating a device for dispensing titrant, electrodes for delivering measuring signals concerning the sample to be analysed, and an evaluation device for evaluating the electrode signals. The electrodes are connected with the evaluation device by means of an exchangeable module containing components for accommodating the titration apparatus to a selected operating mode.

7 Claims, 1 Drawing Figure

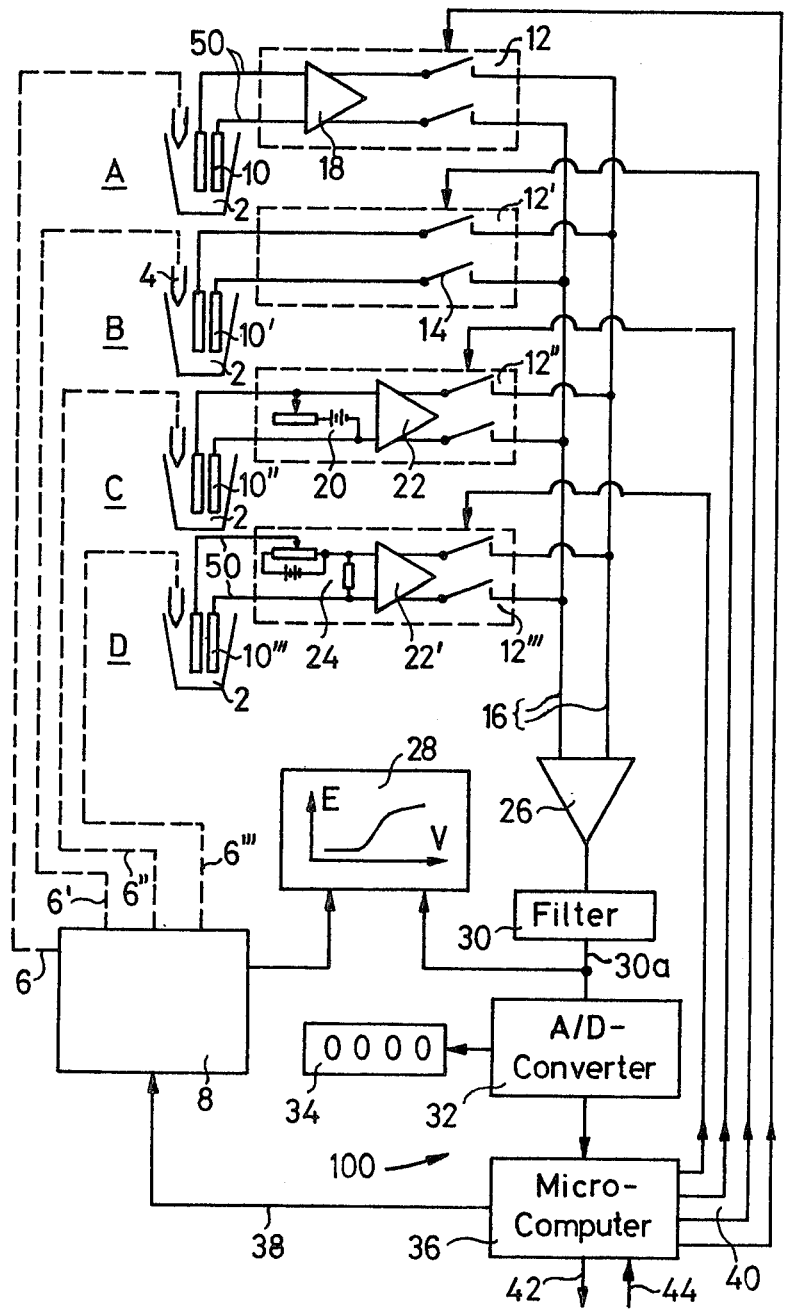

TITRATION APPARATUS

BACKGROUND OF THE INVENTION

The present invention relates to a new and improved construction of titration apparatus or titrator, which is of the type comprising a device for dispensing titrating reagent or titrant, electrodes for delivering signals relevant to the sample undergoing analysis, and an evaluation device for evaluating the delivered electrode signals.

Heretofore when using different operating modes, for instance determining different types of ions, or upon change-over to a different detection method, there were employed individual titrators of appropriate design for carrying out the selected operating mode or method. This was an unsatisfactory solution, especially in those instances where relatively frequently different operating methods or modes were utilized in conjunction with a comparatively low number of total titration runs.

SUMMARY OF THE INVENTION

It is a primary object of the present invention to provide a new and improved construction of titration apparatus which is not afflicted with these limitations and drawbacks.

Another and more specific object of the present invention aims at the provision of novel titration apparatus which makes it possible to avoid the need for individual titrator when carrying out different types of titrations, especially when performing individual titrations or a small series of titrations.

Still another significant object of the present invention aims at the provision of a novel construction of titration apparatus which is designed to increase its versatility as concerns different titration work which can be performed thereat, and specifically, is structured such that it is possible to easily convert the equipment to work with any one of a number of desired titration methods.

Now in order to implement these and still further objects of the invention which will become more readily apparent as the description proceeds, the invention proposes providing for a titration apparatus or titrator of the previously mentioned type a construction wherein the electrodes are operatively connected with the evaluation device by means of an exchangeable module. This module contains components for accommodating the equipment to a selected mode or method of operation.

Therefore, this proposal renders possible performing different types of titrations with one and the same piece of equipment by relatively simple construction thereof, possibly if desired by also allowing for simultaneous exchange of the electrodes.

Each exchangeable module is preferably a plug-in printed circuit. Hence, it is particularly easy to convert the titrator from one mode of operation to another and likewise there can be carried out rapid control thereof and, when necessary, quick exchange of the modules in the event of a defect.

In those instances where a relatively large number of titrations are to be carried out according to different methods, a particularly advantageous constructional manifestation of the invention contemplates providing a multiplicity of electrodes and their associated modules as well as a single evaluation device. Further, with this construction there are provided switching means which allow for the selective connection of a chosen matched set of electrodes-moduleunit with the evaluation device. The correlation of only one evaluation device with a multiplicity of measuring locations or stations affords optimum utilization of the titrator, with exceptionally low costs and equipment expenditure. It is especially advantageous if the evaluation device comprises a microcomputer. With this arrangement and with suitable programming of the microcomputer extensive automatic operation of the titration apparatus is possible.

In principle, the switching means can be of random construction, and thus, for instance there may be provided a manually-operated rotary switch, or, in the case of greater demands with respect to the degree of automation — and of course with a correspondingly increased expenditure or cost — a motor-driven multiposition switch may be provided. There is preferred a solution wherein each module contains a Reed relay. The individual modules can be selectively controlled with comparatively little expenditure in equipment and cost, so that this solution is particularly compatable to automation. Additionally, it has the advantage that certain Reed relays possess high insulation resistance which is particularly desirable in the case of multi-purpose devices, and finally, there is also here present the advantage that the arrangement of the relays at the exchangeable modules, especially in the form of plug-in type modules, increases the operational reliability of the equipment due to the therewith associated easier control- and exchange possibilities.

In the event that the equipment works with high ohmic electrodes, for instance glass electrodes for the pH-measurement, it is advantageous if at least one of the modules contains an impedence converter for amplifying the measured potential. Further embodiments of the invention contemplate that at least one of the modules contains a polarization-current source or a polarization-voltage source.

BRIEF DESCRIPTION OF THE DRAWING

The invention will be better understood and objects other than those set forth above, will become apparent when consideration is given to the following detailed description thereof. Such description makes reference to the annexed drawing wherein the single FIGURE of the drawing schematically illustrates a block circuit diagram of titrator constructed according to the invention.

DETAILED DESCRIPTION OF THE PREFERRED EMBODIMENTS

Describing now the drawings, it is to be understood that only enough of the tritation apparatus or titrator of the invention has been shown herein to enable those skilled in the art to readily understand the underlying principles and concepts of the present invention. To simplify the explanation there has been chosen, by way of example, a titrator using four measuring locations or stations, generally indicated by reference characters A, B, C, and D. These four measuring stations A – D are each symbolized by a respective vessel 2 for the reception of the solution or sample which is to be analysed. Above each vessel 2 there is located a buret tip 4 which is connected through the agency of an associated conduit or line 6, 6', 6'', and 6''' with a multiple buret 8. While for drawing simplification purposes a single buret tip 4 has been shown associated with each vessel or beaker 2, it should be readily apparent and therefore understood to those skilled in the art that each vessel 2 could also have associated therewith a multiplicity of such buret tips, for instance three or four, if the multiple buret 8 is structured to possess a corresponding number of dosing devices. Extending into each vessel 2 is an electrode arrangement, as indicated by the related electrode arrangements 10, 10', 10", and 10'" shown at the measuring positions or stations A, B, C, and D, respectively, and which electrode arrangements are connected by the conductors and lines 50 with their related plug-in type electronic module 12, 12', 12", and 12'" respectively. The plug-in modules preferably consist of printed circuits and are each equipped with a Reed relay 14 serving to selectively establish and interrupt, as desired, the electrical connection between the relevant plug-in module and the common measuring or measurement lines 16. As will be further explained, these plug-in modules may be equipped with additional electronic components. Thus, specifically, as far as the module 12 is concerned there is provided an impedance converter 18, the module 12" is equipped with a polarization-current source 20 at the output side of which there is connected an amplifier 22, and the module 12'" comprises a polarization-voltage source 24, at the output side of which there is connected in circuit the amplifier 22'. For reasons which will be apparent from the description to follow, the module 12' simply is equipped with the Reed relay 14.

Each such Reed relay 14 ensures for reliable disconnection, on the one hand, of the related module which is to be switched-off from the common measuring lines or conductors 16 and, on the other hand, between both of the line branches of the related measuring- and reference electrodes 10, 10', 10", and 10'", as the case may be. The measuring conductors or lines 16 lead to a common measuring amplifier 26, from which location there is delivered the amplified measuring signal by means of a filter 30 to the evaluation device or system, generally indicated by reference character 100. In particular, it will be seen that such signal is delivered from the output side 30a of the filter 30, on the one hand, to a suitable recorder or plotter 28 and, on the other hand, to an analog-digital converter (A/D-converter) 32. The recorder 28 furthermore receives signals from the multiple buret 8 and plots a titration curve, for instance the potential E as a function of the volume V of consumed titrant or titrating reagent.

The digitized signal is delivered, on the one hand, from the analog-digital converter 32 to a digital display 34, and, on the other hand, to a microcomputer 36. Microcomputer 36 is connected by a line 38 with the multiple buret 8 and by means of the further lines or conductors 40 with each of the Reed relays 14. Further, an output 42 of the microcomputer 36 leads to a not particularly illustrated computer which is assigned the task of further processing the measurement results, whereas by means of an input 44 of such computer there are infed the dominant control commands, e.g. program selection and so forth. The microcomputer 36 controls the multiple buret 8 as well as the selection of the desired module which is to be placed into operation.

The illustrated construction of titrator selectively allows the performance of any one of the following:

(a) Potentiometric titration with glass electrodes 10 after switching-in the associated module 12;

(b) Potentiometric titration, during which intermediate amplification of the electrode potential is not required, by selection of the module 12' establishing the direct connection of the electrodes 10' with the common measuring or measurement lines 16, and thus, only acts as a switching module;

(c) Voltametric titration by switching-in the module 12"; and (d) Amperometric titration by switching-in the module 12'".

It should be understood that the design of the modules as well as their number, corresponding to the number of measuring positions or stations, can be conveniently varied as desired. Furthermore, the measuring stations can additionally possess conventional components, such as, for instance, stirrers or thermostats. A system design employing the illustrated measuring amplifier 26 is also not mandatory, and thus, there is possible a variant construction which for instance has each electronic module provided with its own measuring amplifier.

The illustrated exemplary embodiment is particularly suitable for use in complex automated analysis system, especially because through appropriate design of the plug-in electronic modules there can be utilized a common evaluation device or system for different detection methods. This affords considerable economies both in equipment design and hardware expenditure.

While there are shown and described present preferred embodiments of the invention, it is to be distinctly understood that the invention is not limited thereto, but may be otherwise variously embodied and practiced within the scope of the following claims. Accordingly,

What we claim is:

1. A titration apparatus comprising:
   means for dispensing titrant to at least one sample to be analysed;
   a pair of electrodes for delivering signals relevant to the sample undergoing analysis;
   evaluation means for receiving and evaluating the signals delivered by said electrodes;
   an exchangeable module for operatively connecting said electrodes with said evaluation means;
   said exchangeable module containing component means for accommodating the titration apparatus to a selected mode of operation; and
   said exchangeable module comprises a plug-in printed circuit.

2. A titration apparatus comprising:
   means for dispensing titrant to at least one sample to be analysed;
   a multiplicity of pairs of electrodes for delivering signals relevant to the sample undergoing analysis;
   evaluation means for receiving and evaluating the signals delivered by said electrodes;
   a respective exchangeable module for operatively connecting an associated pair of said electrodes with said evaluation means;
   each said exchangeable module containing component means for accommodating the titration apparatus to a selected mode of operation;
   said evaluation means comprising a common evaluation device for said multiplicity of electrode pairs and their associated modules; and
   switching means for operatively connecting a selected set of electrodes and associated module with said evaluation means.

3. The titration apparatus as defined in claim 2, wherein:
   said evaluation means comprises a microcomputer.

4. The titration apparatus as defined in claim 2, wherein:
said switching means comprises a Reed relay provided for each module.

5. The titration apparatus as defined in claim 2, wherein:
said component means of at least one module comprise an impedence converter.

6. The titration apparatus as defined in claim 2, wherein:
the component means of at least one module comprise a polarization-current source.

7. The titration apparatus as defined in claim 2, wherein:
the component means of at least one module comprise a polarization-voltage source.

* * * * *